United States Patent
Badorf et al.

(10) Patent No.: US 6,214,051 B1
(45) Date of Patent: Apr. 10, 2001

(54) FIXATION OF A CERAMIC STRUCTURAL MEMBER BY WAY OF GLIDING IN A FEMORAL PART

(75) Inventors: Dirk Badorf, Frechen; Hartmut Kälberer, Hochdorf; Hans-Georg Pfaff, Ostfildern, all of (DE)

(73) Assignee: CeramTec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/008,427

(22) Filed: Jan. 16, 1998

(30) Foreign Application Priority Data

Jan. 17, 1997 (DE) .............................. 197 01 621
Mar. 20, 1997 (DE) .............................. 197 11 628

(51) Int. Cl.[7] ....................................... A61F 2/38
(52) U.S. Cl. ............................................. 623/20.14
(58) Field of Search ........................ 623/20, 18, 21, 623/16

(56) References Cited

U.S. PATENT DOCUMENTS

| | | | | |
|---|---|---|---|---|
| 4,227,265 | * | 10/1980 | Frey ............................... | 3/1.913 |
| 4,911,721 | * | 3/1990 | Branemark et al. ............ | 623/20 |
| 4,964,869 | * | 10/1990 | Auclair et al. .................. | 623/23 |
| 5,171,282 | * | 12/1992 | Pequignot ....................... | 623/20 |
| 5,197,987 | * | 3/1993 | Koch et al. ..................... | 623/20 |
| 5,356,436 | * | 10/1994 | Nonami et al. ................. | 623/16 |
| 5,645,602 | * | 7/1997 | Albrektsson et al. ........... | 623/20 |
| 5,755,801 | * | 5/1998 | Walker et al. .................. | 623/20 |
| 5,782,925 | * | 7/1998 | Collazo et al. ................. | 623/20 |

FOREIGN PATENT DOCUMENTS

| | | | | |
|---|---|---|---|---|
| 2705885 | * | 12/1994 | (FR) .............................. | 623/20 |
| 1527498 | * | 11/1975 | (IT) .............................. | 623/23 |

* cited by examiner

*Primary Examiner*—Michael J. Milano
*Assistant Examiner*—Alvin Stewart
(74) *Attorney, Agent, or Firm*—Antonelli, Terry, Stout & Kraus, LLP

(57) ABSTRACT

A knee-joint endoprosthesis includes a metallic femoral part (2) anchored in the femur that articulates with a tibial part anchored in the tibia bone, the articulating surface of the femoral part (2) being a ceramic structural member (3) that is connected to the femoral part (2) in a mechanically stable manner.

The attachment of the ceramic structural member (3) to the femoral part (2), can be accomplished by using a conical clamping device, by use of a fixing screw, by shrinking, soldering or welding it on, or by vapor deposition or spray application.

4 Claims, 6 Drawing Sheets

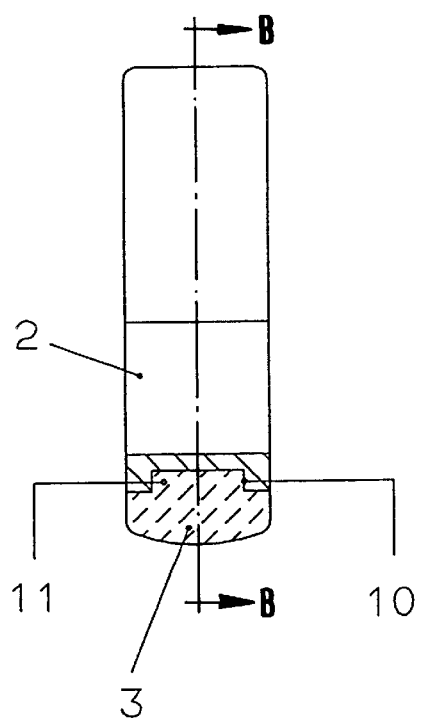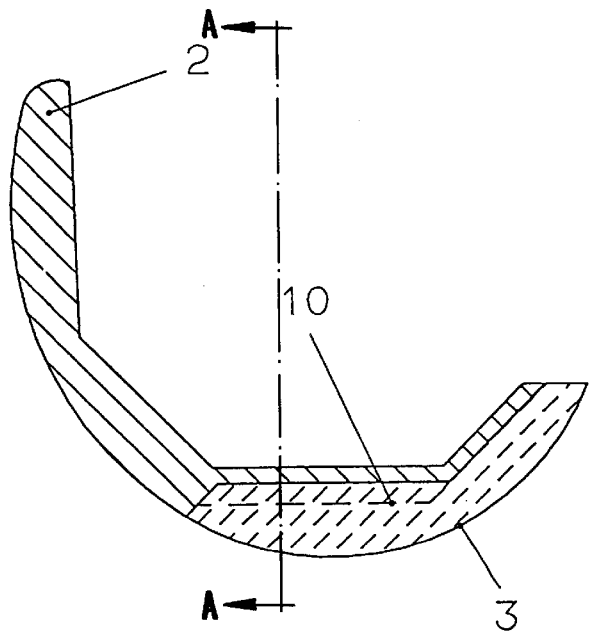

FIXATION OF A CERAMIC STRUCTURAL MEMBER BY WAY OF GLIDING IN A FEMORAL PART

BACKGROUND OF THE INVENTION

The invention relates to a knee-joint endoprosthesis.

Known from WO 95/23567 is a knee-joint endoprosthesis having a metallic femoral part anchored in the femur that articulates with a tibial part made of polyethylene which is anchored in the tibia bone. The articulating surface of the femoral part is formed by a ceramic structural member that is connected to the femoral part in mechanically stable manner.

SUMMARY OF THE INVENTION

The object underlying the invention is to improve a knee-joint endoprosthesis in such a way that the attachment of the ceramic structural member to the femoral part is optimised.

In one embodiment according to the invention the ceramic structural member is anchored on the femoral part by means of a conical clamping device. To this end a conical slot is expediently produced in the femoral part, into which slot the conical lateral surfaces of the structural member are inserted. The angle of the conical clamping device preferably amounts to between 5° and 20°. The larger the angle, the more easily the structural members can be removed during a further operation, even after an implantation.

In a preferred embodiment the conical clamping device is disposed only in the region above what is the loading zone the knee is extended.

In another preferred embodiment the conical clamping device extends over the entire region of the articulating surface.

In an alternative embodiment the structural member is anchored on the femoral part by means of at least one fixing screw. A conical clamping device would be dispensed with in this case.

Use is preferably made of two structural members per endoprosthesis. However, use may also be made of only one structural member, which then has two articulating surfaces.

In another alternative embodiment the ceramic structural member is connected to the femoral part in non-detachable manner by shrinking, soldering or welding. Soldering also includes active soldering.

This attachment can be improved if the ceramic structural member is additionally connected to the femoral part by means of a congruent surface arrangement. The latter may be constituted by, for example, interlocking slots and ribs. In an advantageous configuration, the ceramic structural member is additionally connected to the femoral part by means of a slot/spring connection. The latter is particularly expedient when there is shrinking on. When there is a slot/spring connection, a rib on the structural member, for example, projects into a slot in the femoral part, or vice versa. However, many variants of the congruent surface arrangement are possible.

In another alternative embodiment the ceramic structural member is in the form of a layer and is secured or applied by vapour deposition, spray application or such like. The structural member is accordingly a layer in this case. Of course, this layer may also consist of several individual layers. A ceramic material for the layer or the other structural members would be, for example, aluminium oxide.

BRIEF DESCRIPTION OF THE DRAWINGS

Further features of the invention will emerge from the figures which are described below. Illustrated are.

DETAILED DESCRIPTION OF THE PREFERRED EMBODIMENTS

Figure 1A:
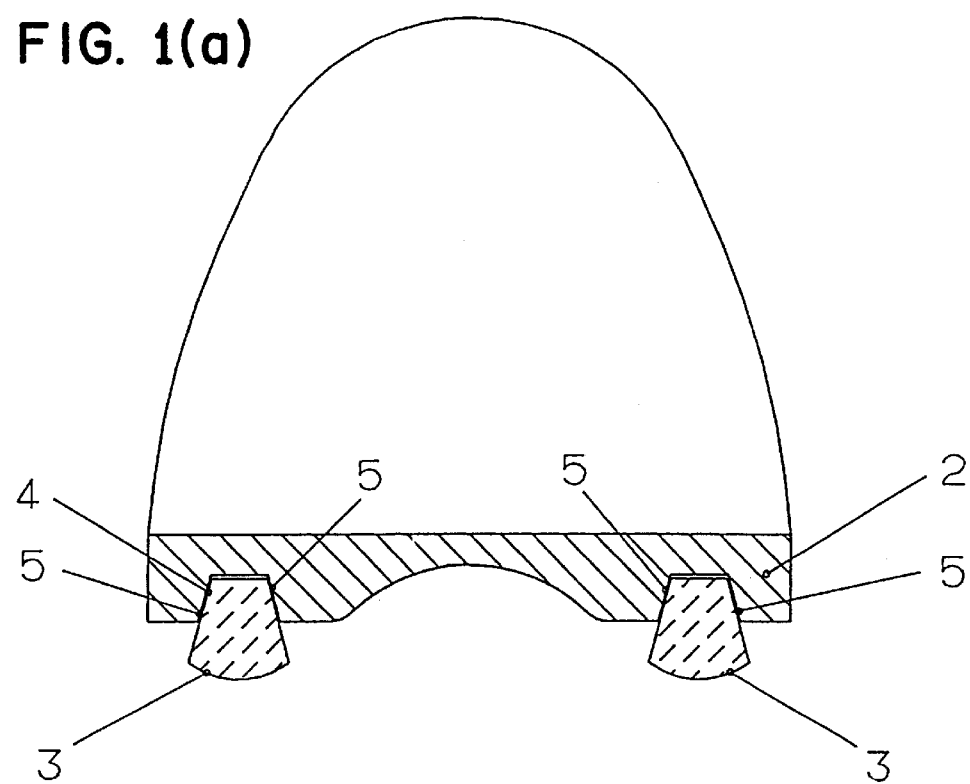
FIG. 1a a cross-section through a femoral part with a structural member inserted with the aid of a conical clamping device, FIG. 1b the same section as in FIG. 1a, but rotated through 180°, FIG. 2 a lateral section through a femoral part with a structural member mounted with the aid of a conical clamping device, the conical clamping device being disposed only above the loading zone, FIG. 3 the attachment of the structural member to the femoral part with the aid of a fixing screw and FIG. 4 the attachment of the structural member to the femoral part by shrinking, FIG. 4a representing a section like FIG. 1b and FIG. 4b representing a section like FIGS. 2, 3.
Figure 1B:
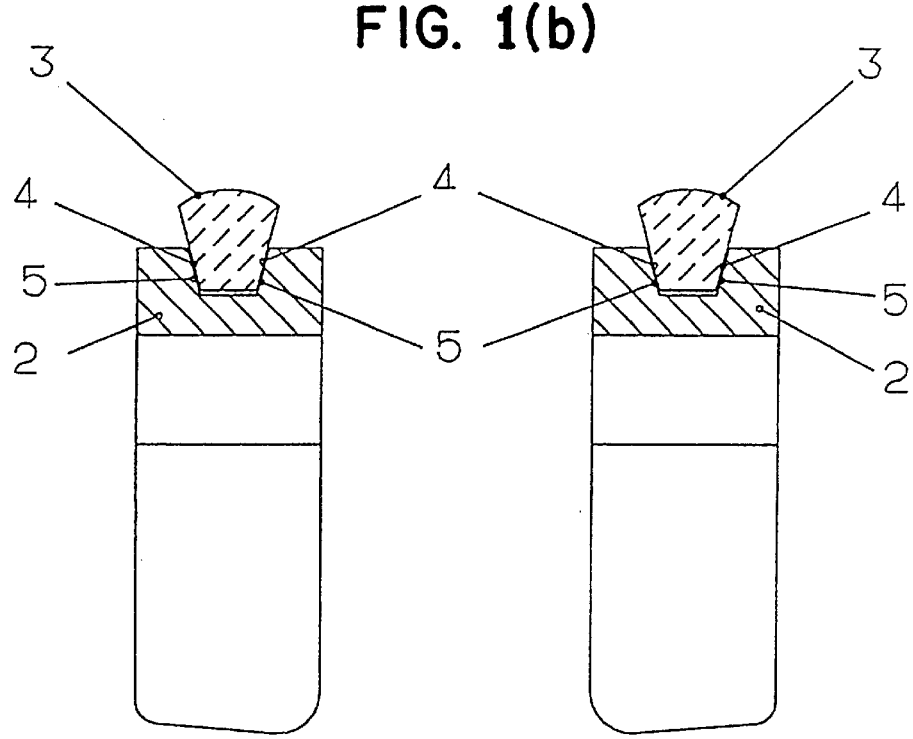

In FIGS. 1a and 1b a metallic femoral part 2 is shown in various sections. A slot 5 or two slots 5 are produced in the femoral part 2 in the region of the articulating surface. At their sides these slots 5 have conical surfaces with angles between 5° and 20°. Enclosed in the slots 5 are ceramic structural members 3 which have corresponding conical lateral surfaces, so that a conical clamping device 4 is formed. The structural members 3 are not shown articulating with a tibial part anchored in the tibia bone. In this embodiment the slot 5 extends along the entire articulating surface. However, several slots 5 or individual notches may also be provided so that the structural member 3 is anchored to the femoral part 2 only at individual points by means of a conical clamping device 4.

Figure 1C:
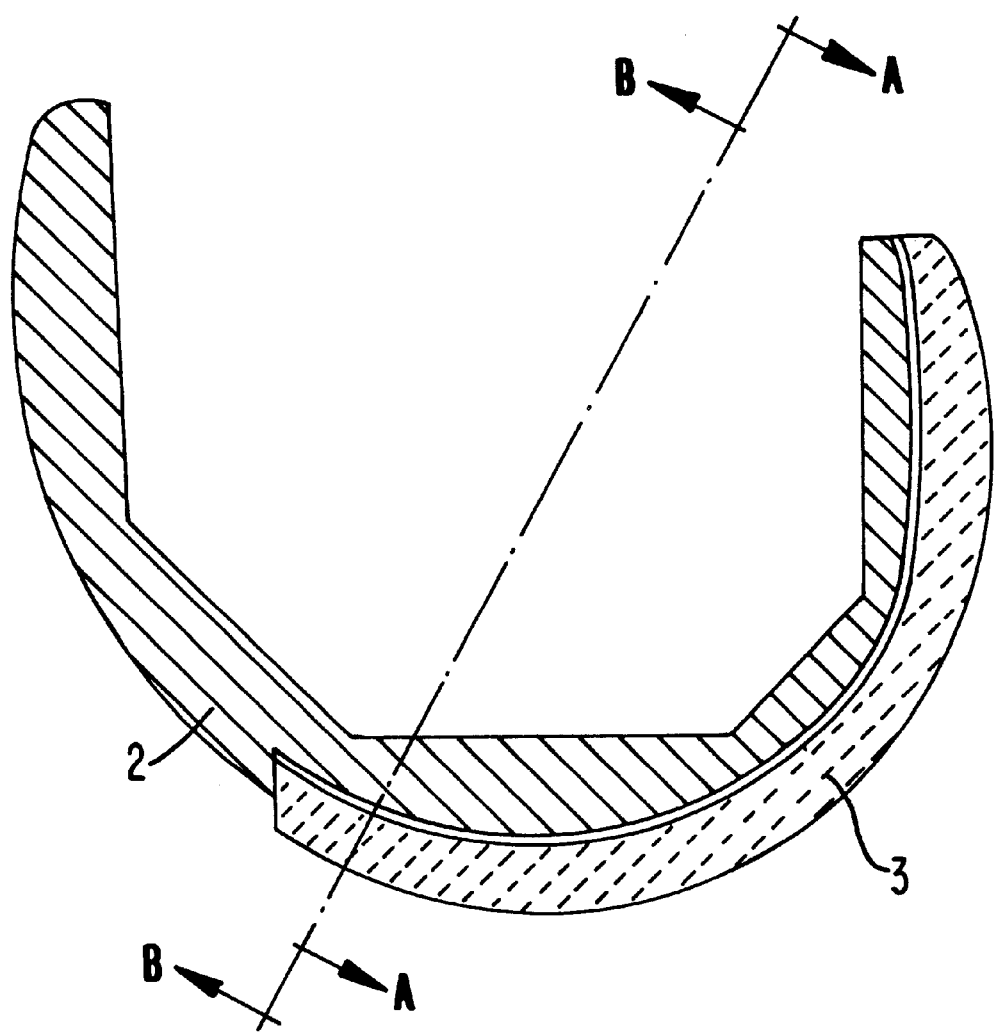
Figure 2:
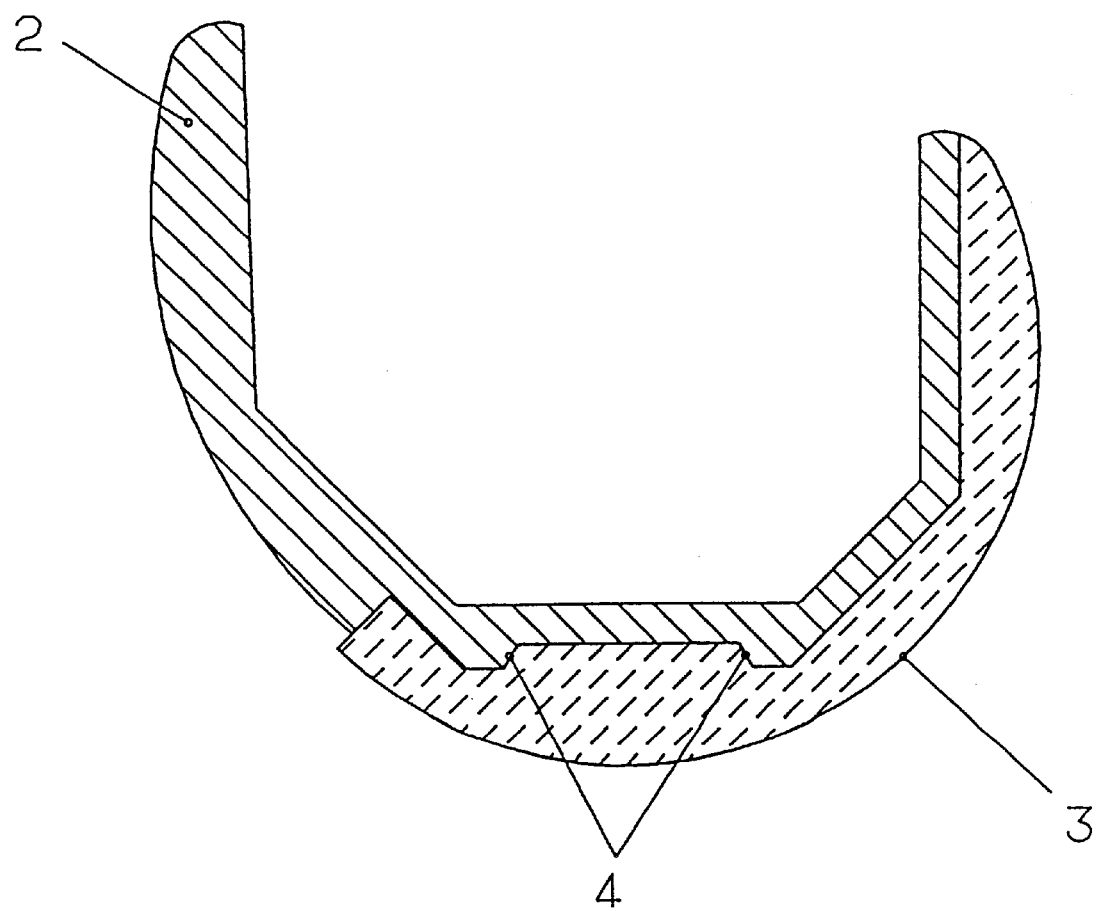

FIG. 2 shows a lateral section through a femoral part 2 with, likewise, a structural member 3 that is mounted with the aid of a conical clamping device 4. The conical clamping device 4 in this case, as distinct from the embodiment of FIG. 1, is disposed only above what is the loading zone when the knee is extended. To this end a clamping surface that is not as large as that in FIG. 1 is produced in the femoral part 2.

Figure 3:
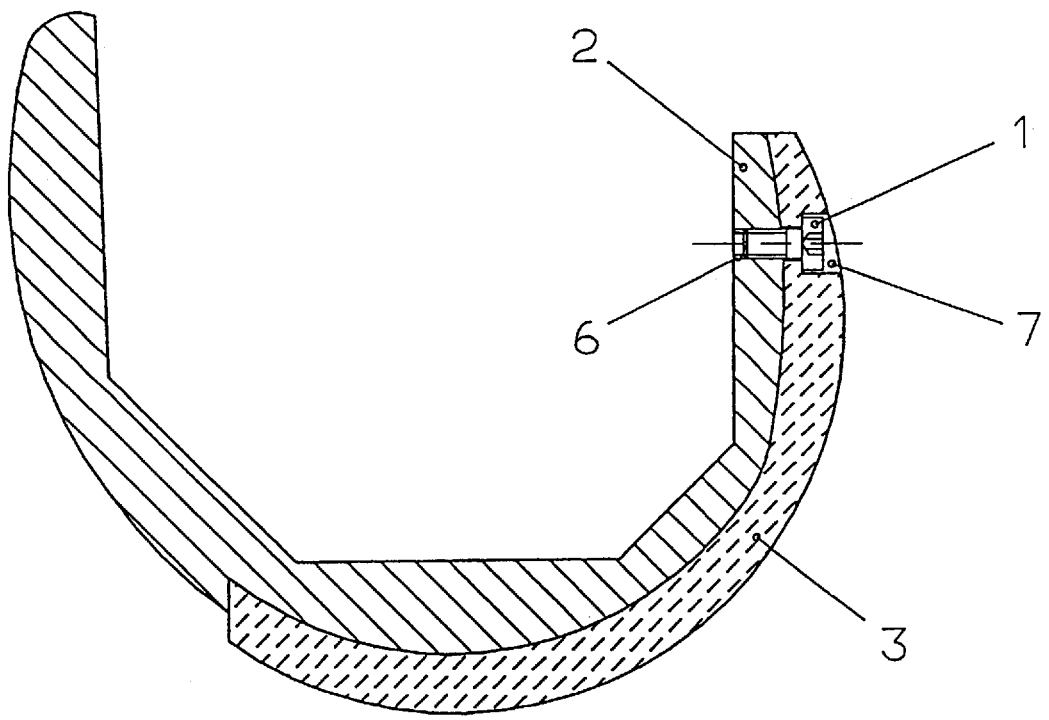
Figure 5:
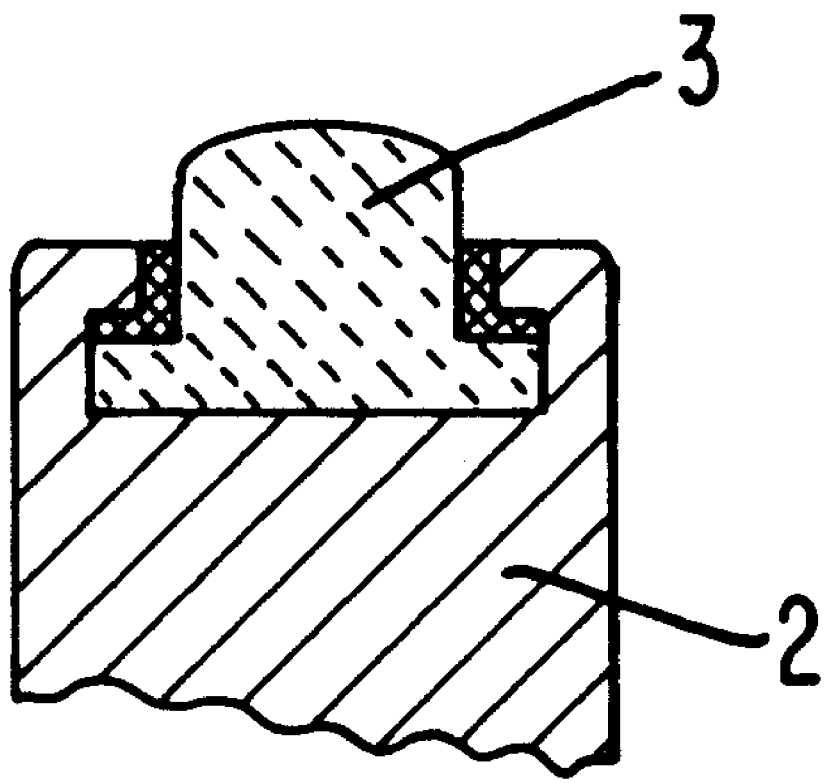

FIG. 3 shows the attachment of the ceramic structural member 3 to the femoral part 2 by means of a fixing screw 1. To this end a bore 7 is disposed in the structural member 3 and a thread 6 is disposed in the femoral part 2. The fixing screw 1 projects through the bore 7 into the thread 6 and in this way anchors the structural member 3 to the femoral part 2.

If necessary, several fixing screws can also be used, which are advantageously disposed sunk in the structural member 3.

FIG. 4 shows a femoral part 2 that has a slot 10 on its tibial side. The associated ceramic structural member 3 has a rib 11 that is congruent with the slot. FIG. 4a shows the femoral part 2 in cross-section and FIG. 4b shows it in longitudinal section. The structural member 3 is attached by shrinking it on. But it may also be soldered on or welded on. In this case the slot/spring connection may optionally be dispensed with.

What is claimed is:

1. Knee-joint endoprosthesis comprising a metallic femoral part anchored in the femur that articulates with a tibial part anchored in the tibia bone, the articulating surface of the femoral part being a ceramic structural member that is connected to the femoral part in a mechanically stable manner, wherein the ceramic structural member is anchored on the femoral part by means of a conical clamping device which extends over the entire region of the articulating surface wherein the conical clamping device comprises a conical slot in the femoral part, and conical lateral surfaces on the ceramic structural member, the conical slot having tapering lateral surfaces such that the conical slot becomes wider at an outside of the slot and narrower at an interior of the slot, and the conical lateral surfaces of the structural member being inserted in the conical slot.

2. Knee-joint endoprosthesis according to claim 1, wherein the angle of the conical clamping device amounts to between 5° and 20°.

3. Knee-joint endoprosthesis according to claim 1, wherein two structural members are used per knee-joint endoprosthesis.

4. Knee-joint endoprosthesis according to claim 1, wherein femoral part has a median part a branched end, and wherein the ceramic structural member extends to an end of the median part opposite the branched end.

* * * * *